United States Patent [19]

Chou

[11] 4,194,982
[45] Mar. 25, 1980

[54] N-SULFONYLATED POLYALKENYLSUCCINIMIDE AND LUBRICANT COMPOSITION

[75] Inventor: Kechia J. Chou, Wappingers Falls, N.Y.

[73] Assignee: Texaco Inc., White Plains, N.Y.

[21] Appl. No.: 921,691

[22] Filed: Jul. 3, 1978

[51] Int. Cl.² ............................................. C10M 1/38
[52] U.S. Cl. ........................... 252/47.5; 252/32.7 E; 260/326.5 SF; 260/326.5 FM
[58] Field of Search ............ 252/32.7 E, 47.5, 51.5 A; 260/326.5 SF, 326.5 FM

[56] References Cited

U.S. PATENT DOCUMENTS

| 3,309,316 | 3/1967 | McNinch et al. | 252/47.5 |
|---|---|---|---|
| 3,470,098 | 9/1969 | O'Halloran | 252/47.5 |
| 3,574,194 | 4/1971 | Pfirrmann | 260/326.5 SF X |
| 3,725,434 | 4/1973 | Elliott et al. | 252/47.5 X |
| 3,775,401 | 11/1973 | Pfirrmann | 260/326.5 SF X |
| 3,789,056 | 1/1974 | Pfirrmann | 260/326.5 SF X |
| 3,813,387 | 5/1974 | Pfirrmann et al. | 260/326.5 SF X |
| 4,122,266 | 10/1978 | de Vries | 252/47.5 X |

FOREIGN PATENT DOCUMENTS 1598564  8/1970 France ............................ 260/326.5 SF Primary Examiner—Andrew Metz
Attorney, Agent, or Firm—Thomas H. Whaley; Carl G. Ries; James J. O'Loughlin

[57] ABSTRACT

An N-sulfonylated hydrocarbon-substituted succinimide represented by the formula:

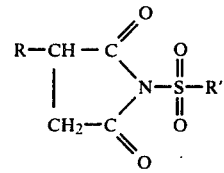

in which R and R' are hydrocarbon radicals and a lubricating oil composition for an internal combustion engine containing an N-sulfonylated hydrocarbon-substituted succinimide.

13 Claims, No Drawings

4,194,982

N-SULFONYLATED POLYALKENYLSUCCINIMIDE AND LUBRICANT COMPOSITION

BACKGROUND OF THE INVENTION

1. Field of the Invention

This invention lies in the field of art relating to a lubricant additive and a lubricating oil composition adapted for use between a plurality of moving surfaces with which the fluid composition is in contact with the purpose of reducing the friction between these surfaces and to provide protection from wear and corrosion. Lubricant compositions tend to deteriorate under the conditions of use. This is particularly true for a lubricant employed in an internal combustion engine where such use results in the formation of sludge, lacquer and carbonaceous or resinous materials which adhere to the engine parts, particularly the piston rings, groves and skirts, and cylinder walls thus reducing the operating efficiency of the engine. To counteract the formation of these deposits and/or to ameliorate the effects of such deposits, certain chemical additives have been found which, when added to the lubricating oil, have the ability to minimize the formation of the deposits or to maintain the deposits formed suspended in the oil so that the engine is kept clean and in an efficient operating condition for extended periods of time. These agents are known in the art to which this invention pertains as detergents, dispersants or detergent-dispersants. Metal organic compounds are particularly useful in this respect and they are exemplified by the oilsoluble zinc, calcium and barium salts of petroleum sulfonic acids, alkylated hydroxybenzoic acids, dialkyldithiophosphoric acids and the like.

There are drawbacks associated with the use of an organic metal salt in a lubricating oil composition for an internal combustion engine. A major drawback is that the metal salts formed by neutralization of the acids resulting from the combustion process are generally insoluble in the lubricating oil composition. More importantly these insoluble metal salts occur as hard deposits on the piston rings, piston skirts or the cylinder liners and in the ring grooves of the engine. These hard deposits are believed to be a major contributor to the wear that is experienced in an internal combustion engine. This problem is particularly acute with compression ignition engines, such as a diesel engine, wherein the engine oil is subjected to extremely high temperature and compression stresses. This invention also pertains to a method for lubricating an internal combustion engine which comprises supplying to the lubricating system of the engine the novel lubricating oil composition described hereinabove.

The novel lubricant and method of lubricating of this invention is most efficacious when employed in a compression ignition engine such as a diesel engine, wherein the lubricating oil composition is subjected to extreme temperature and compression stresses including engine oil temperature above about 600° F. which conditions are particularly prone to promote the formation of hard engine deposits.

2. Description of the Prior Art

The use of metal organic salts in a crankcase engine oil is disclosed in U.S. Pat. Nos. 3,528,917, 3,761,414, 3,969,235, 3,474,035 and 3,706,632. These disclosures are incorporated in the disclosure of this application.

A copending application Ser. No. 796,915 filed on May 16, 1977 discloses a lubricating oil composition containing a hydrocarbon-substituted succinimide ether which is effective for modifying or softening the deposits formed in an internal combustion engine.

SUMMARY OF THE INVENTION

The novel additive of the invention is N-sulfonylated hydrocarbon-substituted succinimide represented by the formula:

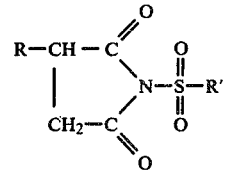

in which R is a hydrocarbon radical having from about 1 to 40 carbon atoms and R' is a hydrocarbon radical having from about 6 to 20 carbon atoms.

The lubricating oil composition of the invention comprises a hydrocarbon oil of lubricating viscosity, a metal-containing additive characterized by promoting the formation of hard deposits in an internal combustion engine and an effective deposit-softening amount of a novel N-sulfonylated succinimide described hereinabove.

This invention is also directed to a method for lubricating an internal combustion engine and comprises supplying to the crankcase and lubricating system of the engine, a lubricating oil composition comprising a major portion of a hydrocarbon oil of lubricating viscosity, a minor amount of a metal-containing additive characterized by promoting the formation of hard deposits in an internal combustion engine and an effective deposit-softening amount of the prescribed N-sulfonylated hydrocarbon-substituted succinimide.

DETAILED EMBODIMENT OF THE INVENTION

The novel N-sulfonylated hydrocarbonsubstituted succinimide additive of the invention is prepared by reacting a hydrocarbon-substituted succinimide with a hydrocarbon sulfonylchloride as illustrated by the following formulas:

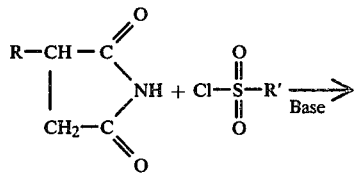

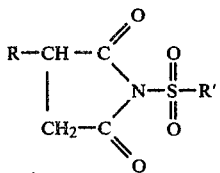

in which R is a hydrocarbon radical having from about 1 to 40 carbon atoms and R' is a hydrocarbon radical having from about 6 to 20 carbon atoms. In the preferred reaction, approximately equimolar amounts of the hydrocarbon substituted succinimide and of the hydrocarbon sulfonyl chloride are employed. However, other ratios of the reactants may be employed as, for example, from about 0.75 to 1.25 moles of the hydrocarbon-substituted sulfonyl chloride per mole of the hydrocarbon-substituted succinimide.

The starting hydrocarbon-substituted succinimide is represented by the following formula:

$$\begin{array}{c} R-CH-C \overset{O}{\underset{}{\diagup}} \\ | \qquad \qquad \diagdown NH \\ CH_2-C \underset{}{\diagup} \\ \qquad \qquad \diagdown O \end{array}$$

in which R is a hydrocarbon radical having from about 1 to about 40 carbon atoms. Preferably, R is an aliphatic hydrocarbon radical having from about 6 to 30 carbon atoms. In a more preferred reaction, R represents an alkenyl hydrocarbon radical. Desirably R is an alkenyl radical having from about 8 to 20 carbon atoms.

Examples of suitable hydrocarbon-substituted succinimide reactants include tetrapropenyl succinimide, decenyl succinimide, tripropenyl succinimide, diisobutenylsuccinimide pentapropenylsuccinimide and the corresponding saturated hydrocarbon-substituted succinimides.

The hydrocarbon sulfonyl halide reactant is represented by the formula:

$$\begin{array}{c} O \\ \| \\ X-S-R' \\ \| \\ O \end{array}$$

in which X represents a halogen such as the chloride ion bromide ion or iodide ion and R' represents a hydrocarbon radical having from about 6 to 20 carbon atoms. The preferred hydrocarbon sulfonyl halide reactants are those in which the halide is chloride and the hydrocarbon radical represented by R' has from about 7 to 16 carbon atoms. Still more preferred reactants are the aryl sulfonyl chlorides in which R' represents an aryl radical or a hydrocarbon-substituted aryl radical having from about 7 to 10 carbon atoms.

Suitable hydrocarbon sulfonyl halide reactants include p-toluenesulfonylchloride, o, m, and p-toluenesulfonyl bromide, benzenesulfonyl chloride, benzenesulfonyl iodide and o, m, and p-xylenesulfonyl chloride and bromide.

Suitable bases which can be employed include sodium hydride, pyridine, and triethylamine.

The following examples illustrate the preparation of the novel additive of the invention.

EXAMPLE I

N-Tosyltetrapropenylsuccinimide

A mixture of tetrapropenylsuccinimide (77 mmol), toluene (100 ml) and pyridine (10 ml) was stirred at room temperature for 1 hr. A solution of 75 m mol of p-toluenesulfonyl chloride in 20 ml of ether was added to the above mixture. After the addition, the mixture was heated to reflux for 4 hours. The precipitate was filtered off and the filtrate was washed with water (200 ml) and dried over over anhydrous magnesium sulfate. The drying agent was filtered off and the solvent was removed in a water aspirator to give 17.6 g (56%) of a brown viscous oil. Infrared analysis (1706, 1302 1170 cm$^{-1}$) showed the product to be N-tosyltetrapropenylsuccinimide corresponding to the formula:

$$\begin{array}{c} \text{tetrapropenyl}-CH-C \overset{O}{\underset{}{\diagup}} \\ | \qquad \qquad \diagdown \underset{O}{\overset{O}{\underset{\|}{N-S}}}-\!\!\bigcirc\!\!-CH_3 \\ CH_2-C \underset{}{\diagup} \\ \qquad \qquad \diagdown O \end{array}$$

EXAMPLE II

N-Benzenesulfonyltetrapropenylsuccinimide

A mixture of tetrapropenylsuccinimide (113 m mol), toluene (100 ml) and pyridine (30 ml) was stirred at room temperature for 1 hr. A solution of benzene sulfonyl chloride (113 mmol) in 50 ml toluene was added to the above mixture. After the addition, the mixture was heated to reflux for 4 hours. The precipitate was filtered off and the filtrate was washed with water (200 ml) and dried over anhydrous magnesium sulfate. The drying agent was filtered off and the solvent was removed in a water aspirator to give 28.7 g (63%) of a brown oil. Infrared analysis (1706, 1294, 1165 cm$^{-1}$ of the product indicated it to be N-benzenesulfonyltetrapropenylsuccinimide represented by the formula:

$$\begin{array}{c} \text{tetrapropenyl}-CH-C \overset{O}{\underset{}{\diagup}} \\ | \qquad \qquad \diagdown \underset{O}{\overset{O}{\underset{\|}{N-S}}}-\!\!\bigcirc \\ CH_2-C \underset{}{\diagup} \\ \qquad \qquad \diagdown O \end{array}$$

Other effective N-sulfonylated hydrocarbon-substituted succinimides include:

N-xylylsulfonyl tetrapropenylsuccinimide
N-benzenesulfonyl pentapropenylsuccinimide
N-benzenesulfonyl octadecylsuccinimide
N-tolylsulfonyl decylsuccinimide The lubricant composition of the invention employs as its base a petroleum or mineral oil of lubricating viscosity. The base oil may consists of a paraffinic base, a naphthenic base or a mixed paraffinic-naphthenic base oil. In general, the mineral oil base will have a viscosity at 100° F. ranging from about 50 to 1000 with the preferred range being from 70 to 300.

An essential feature of the lubricant of the invention is the presence of an organic-metal-containing lubricant additive which under the conditions of use promotes the formation of hard depostis in an internal combustion engine. The most harmful lubricating oil additives in this respect are the organic zinc compounds, such as the zinc hydrocarbyl dithiophosphates.

Other conventional organic metal-containing lubricating oil additives which may promote hard deposits in an internal combustion engine include calcium or magnesium-containing phenolates or sulfonates.

The improvement of reducing deposits hardness caused by a lubricating oil composition was demonstrated in a bench test and in an engine test in which the hardness of the deposits produced was measured against comparison lubricants. Hardness is reported as the Knoop Hardness Number, the higher number indicating increasingly harder deposits.

A Base Oil employed in the examples was a blend of paraffinic mineral oils having the following inspection tests.

| | |
|---|---|
| Gravity °API | 27.2 |
| Viscosity, SUS at | |
| 100° F. | 849 |
| 210° F. | 78.6 |

This Base Oil was blended with a conventional organic metal containing additive to form the following blend, parts given in weight percent.

| BASE BLEND A | |
|---|---|
| Base Oil, % | 99.0 |
| Zinc dialkyldithiophosphate[1] | 1.0 |

[1]Prepared by reacting 2.7 moles of an alcohol mixture (consisting of 70% heptanols, 10% hexanols, 10% octanols and 10% butanols and minor components), 2.3 moles of isopropanol and 1.0 mole $P_2S_5$ in a conventional manner and then reacting the dialkyldithiophosphonic acid with an excess of zinc oxide to form the zinc dialkyldithiophosphate.

Base Blend B was a conventional diesel engine oil. It contained a calcium carbonate overbased (300 TBN, Total Base Number) calcium sulfonate, an overbased (5 TBN) calcium sulphonate, a 2/1 overbased sulfurized calcium alkylphenolate, a zinc dialkyl-dithiophosphate and a zinc diaryldithiophosphate in addition to a conventional dispersant, rust inhibitor and foam inhibitor. Its inspection values were as follows:

| | |
|---|---|
| Gravity, API | 27.7 |
| Viscosity, SUS at | |
| 100° F. | 515 |
| 210° F. | 72.2 |
| % Phosphorus | 0.22 |
| % Calcium | 0.24 |
| % Zinc | 0.11 |

The oil compositions of the invention as well as the comparison oil were employed under deposit forming conditions in a bench test and in an engine test in order to evaluate the effectiveness of the lubricating oil composition of the invention. In the bench test, a burner nozzler was positioned midway inside of a six inch heat shielded well which rested on a hot plate as a source of heat. An aluminum panel was placed at the bottom of the well three inches below the vertically positioned, downwardly directed nozzle. The temperature of the aluminum panel was controlled by a thermocouple.

In operation, the temperature of the aluminum panel was tested at from 650°–700° F. The test oil was passed through the nozzle at a rate of 8 liters per minute in conjunctions with an air jet. This test was run for a period of 2 hours. On completion of this high temperature oil oxidation run, the aluminum panel with the adhering oil deposits was cooled. The deposits formed were removed from the panel and their hardness determined.

In the engine test, a Caterpillar-1-G engine was used with the test oil employed as the crankcase lubricant for this engine. This engine was operated under standard operating conditions for a period of 180 hours. On completion of the running time, the engine was dissembled and the deposits formed were from the fireland, piston rings, grooves and skirts and from the cylinder walls and their hardness determined.

The effectiveness of the deposit softening additive of the invention was determined by adding same to the foregoing Base Blends and comparing the results in the above described Bench and Caterpillar Engine Tests. The results are given in Table I and II below.

TABLE I

| | Deposits from Bench Test | | | |
|---|---|---|---|---|
| | | | Knoop Hardness Numbers[a] Rating Deposits at | |
| Run | Lubricant | wt. % | 650°–680° F. | 700° F. |
| 1 | Base Oil A | 100 | 268–355 | 355–384 |
| 2 | Base Oil A | 98 | 194–227 | 194–227 |
| | Example I Additive | 2 | | |

[a]Knoop Hardness Numbers were determined by direct comparison to standard specimens of known hardness.

TABLE II

| | Caterpillar I-G Engine Test | | | | |
|---|---|---|---|---|---|
| | | | Knoop Hardness Numbers Rating | | |
| Run | Lubricant | wt. % | Top Ring Groove | Fireland | Total Wt. Dem. |
| 3 | Base Oil B | 100 | 268–355 | 355–384 | 265 |
| 4 | Base Oil B | 98 | 227–268 | 227–268 | 204 |
| | Example I additive | 2 | | | |

Both the Bench test and the Engine Test demonstrate that there was a substantial reduction in the hardness of the deposits formed when the lubricating oil composition of the invention was employed in these tests. This discovery was unexpected and it provides a novel solution to the problem of reducing or ameliorating engine wear in an internal combustion engine.

I claim:

1. An N-sulfonylated succinimide represented by the formula:

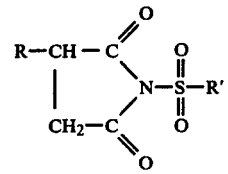

in which R is an aliphatic hydrocarbon radical having from 1 to 40 carbon atoms and R' is a hydrocarbon radical having from about 6 to 20 carbon atoms.

2. A compound according to claim 1 in which R is an aliphatic hydrocarbon radical having from about 6 to 20 carbon atoms and R' is a hydrocarbon radical having from about 7 to 16 carbon atoms.

3. A compound according to claim 1 in which R is an alkenyl radical and R' is an aryl radical.

4. A compound represented by the formula:

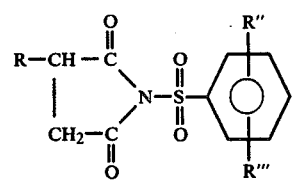

in which R is an aliphatic hydrocarbon radical having from about 8 to 20 carbon atoms and R" and R'" each represent hydrogen or an aliphatic hydrocarbon radical having from 1 to 8 carbon atoms.

5. N-tosyltetrapropenylsuccinimide.

6. N-benzenesulfonyltetrapropenylsuccinimide.

7. N-dimethylbenzenesulfonyltripropenylsuccinimide.

8. A lubricating oil composition comprising a major portion of a hydrocarbon oil of lubricating viscosity, a minor amount of a metal-containing additive characterized by promoting the formation of hard deposits in an internal combustion engine and an effective deposit modifying amount of an N-sulfonylated hydrocarbon substituted succinimide represented by the formula:

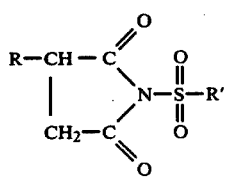

in which R is an aliphatic hydrocarbon radical having from about 1 to 40 carbon atoms and R' is a hydrocarbon radical having from about 6 to 20 carbon atoms.

9. A lubricating oil composition according to claim 8 in which R is an aliphatic hydrocarbon radical having from about 6 to 30 carbon atoms and R' is a hydrocarbon radical having from about 7 to 16 carbon atoms.

10. A lubricating oil composition according to claim 8 in which R is an alkenyl radical and R' is an aryl radical.

11. A lubricating oil composition according to claim 8 containing from about 0.01 to 10 weight percent of said succinimide.

12. A lubricating oil composition according to claim 8 in which said succinimide is N-tosyltetrapropenyl succinimide.

13. A lubricating oil composition according to claim 8 in which said succinimide is N-benzenesulfonyl tetrapropenylsuccinimide.

* * * * *